(12) United States Patent
Thomas et al.

(10) Patent No.: US 9,192,476 B2
(45) Date of Patent: Nov. 24, 2015

(54) PYROLYTIC CARBON IMPLANTS WITH POROUS FIXATION COMPONENT AND METHODS OF MAKING THE SAME

(71) Applicant: Zimmer, Inc., Warsaw, IN (US)

(72) Inventors: Brian H. Thomas, Auburndale, FL (US); Oludele O. Popoola, Granger, IN (US); Joseph R. Vargas, Garnerville, NY (US); Steven Seelman, Montclair, NJ (US); Jeffrey P. Anderson, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/197,689

(22) Filed: Mar. 5, 2014

(65) Prior Publication Data

US 2014/0188244 A1    Jul. 3, 2014

Related U.S. Application Data

(63) Continuation of application No. 13/246,544, filed on Sep. 27, 2011, now abandoned.

(60) Provisional application No. 61/387,678, filed on Sep. 29, 2010.

(51) Int. Cl.
*A61F 2/30* (2006.01)
*A61F 2/28* (2006.01)
(Continued)

(52) U.S. Cl.
CPC ............... *A61F 2/30767* (2013.01); *A61F 2/28* (2013.01); *A61F 2/30* (2013.01); *A61F 2/32* (2013.01); *A61F 2/34* (2013.01); *A61F 2/36* (2013.01); *A61F 2/3603* (2013.01); *A61F 2/38* (2013.01); *A61F 2/4003* (2013.01); *A61F 2/42* (2013.01); *A61F 2/44* (2013.01); *A61F 2002/3008* (2013.01); *A61F 2002/30011* (2013.01); *A61F 2002/3092* (2013.01); *A61F 2002/3098* (2013.01); *A61F 2002/30138* (2013.01); *A61F 2002/30143* (2013.01);
(Continued)

(58) Field of Classification Search
CPC .................................................. A61F 2/30767
USPC ............................. 427/2.26, 282; 623/18.11
See application file for complete search history.

(56) References Cited

U.S. PATENT DOCUMENTS 3,526,906 A  9/1970  De Laszlo
3,623,164 A  11/1971  Bokros
(Continued)

FOREIGN PATENT DOCUMENTS

DE   19517843 A1   11/1996
EP   0001147 A1    3/1979
(Continued)

OTHER PUBLICATIONS

Implex Corp. The Hedrocel Trabecular Metal Reconstructive System. Oct. 2003 retieved from http://www.accessdata.fda.gov/cdrh_docs/pdf3/k032344.pdf.*

(Continued)

*Primary Examiner* — Cachet Sellman
(74) *Attorney, Agent, or Firm* — Schwegman Lundberg & Woessner, P.A.

(57) ABSTRACT

An orthopedic implant including an articulation portion having a pyrolytic carbon bearing surface and a porous bone on- or in-growth structure, and methods of making the same.

23 Claims, 8 Drawing Sheets

(51) Int. Cl.
  *A61F 2/32* (2006.01)
  *A61F 2/34* (2006.01)
  *A61F 2/36* (2006.01)
  *A61F 2/38* (2006.01)
  *A61F 2/40* (2006.01)
  *A61F 2/42* (2006.01)
  *A61F 2/44* (2006.01)

(52) U.S. Cl.
  CPC ............... *A61F 2002/30878* (2013.01); *A61F 2002/30981* (2013.01); *A61F 2310/00161* (2013.01); *A61F 2310/00395* (2013.01); *A61F 2310/00574* (2013.01); *Y10T 156/10* (2015.01)

(56) References Cited

U.S. PATENT DOCUMENTS

| | | | |
|---|---|---|---|
| 3,707,006 A * | 12/1972 | Bokros et al. | 424/422 |
| 3,893,196 A | 7/1975 | Hochman | |
| 3,926,567 A | 12/1975 | Fletcher | |
| 4,012,796 A | 3/1977 | Weisman | |
| 4,126,924 A | 11/1978 | Akins et al. | |
| 4,166,292 A | 9/1979 | Bokros | |
| 4,457,984 A | 7/1984 | Otani et al. | |
| 4,718,905 A | 1/1988 | Freeman | |
| 4,846,834 A | 7/1989 | Von Recum | |
| 5,198,308 A | 3/1993 | Shetty et al. | |
| 5,282,861 A * | 2/1994 | Kaplan | 623/23.51 |
| 5,534,033 A | 7/1996 | Simpson | |
| 5,593,445 A * | 1/1997 | Waits | 623/23.42 |
| 5,671,322 A * | 9/1997 | Finicle | 392/389 |
| 5,981,827 A | 11/1999 | Devlin et al. | |
| 6,090,145 A | 7/2000 | Hassler | |
| 6,217,616 B1 | 4/2001 | Ogilvie | |
| 6,436,146 B1 | 8/2002 | Hassler et al. | |
| 7,641,696 B2 | 1/2010 | Ogilvie et al. | |
| 7,837,739 B2 | 11/2010 | Ogilvie | |
| 2005/0171604 A1 | 8/2005 | Michalow | |
| 2005/0246032 A1* | 11/2005 | Bokros et al. | 623/23.6 |
| 2007/0123993 A1 | 5/2007 | Hassler et al. | |
| 2007/0156250 A1 | 7/2007 | Seitz, Jr. et al. | |
| 2007/0225822 A1 | 9/2007 | Santilli et al. | |
| 2008/0195221 A1 | 8/2008 | Howald et al. | |
| 2008/0274372 A1 | 11/2008 | Gillesberg et al. | |
| 2009/0036995 A1 | 2/2009 | Lozier et al. | |
| 2009/0098310 A1 | 4/2009 | Hippensteel et al. | |
| 2009/0143865 A1 | 6/2009 | Hassler et al. | |
| 2009/0192610 A1 | 7/2009 | Case et al. | |
| 2009/0240336 A1 | 9/2009 | Vander Meulen et al. | |
| 2010/0063593 A1 | 3/2010 | Klawitter | |
| 2010/0094292 A1 | 4/2010 | Parrott | |
| 2010/0268337 A1 | 10/2010 | Gordon et al. | |
| 2010/0324691 A1 | 12/2010 | Brunnarius | |
| 2010/0324694 A1 | 12/2010 | Hassler et al. | |
| 2010/0331990 A1 | 12/2010 | Mroczkowski et al. | |
| 2011/0009973 A1 | 1/2011 | Meyers et al. | |
| 2011/0015740 A1 | 1/2011 | Metzger et al. | |
| 2011/0054631 A1 | 3/2011 | Ratron et al. | |
| 2012/0101592 A1 | 4/2012 | Thomas et al. | |
| 2012/0158139 A1* | 6/2012 | Liu | 623/16.11 |
| 2013/0304226 A1* | 11/2013 | Ritz et al. | 623/23.5 |

FOREIGN PATENT DOCUMENTS

| | | |
|---|---|---|
| EP | 0055406 B1 | 3/1985 |
| EP | 0269745 A1 | 6/1988 |
| EP | 0447744 A2 | 9/1991 |
| EP | 0560279 A1 | 9/1993 |
| FR | 2566272 A1 | 12/1985 |
| FR | 2928829 A1 | 9/2009 |
| WO | WO-0141826 A1 | 6/2001 |
| WO | WO-2009115616 A1 | 9/2009 |
| WO | WO-2012050837 A1 | 4/2012 |

OTHER PUBLICATIONS

U.S. Appl. No. 13/246,544 , Response filed Sep. 19, 2013 to Non Final Office Action mailed Jun. 19, 2013, 12 pgs.
U.S. Appl. No. 13/246,544, Final Office Action mailed Jan. 6, 2014, 13 pgs.
U.S. Appl. No. 13/246,544, Non Final Office Action mailed Jun. 19, 2013, 11 pgs.
U.S. Appl. No. 13/246,544, Response filed May 6, 2013 to Restriction Requirement mailed Mar. 29, 2013, 5 pgs.
U.S. Appl. No. 13/246,544, Restriction Requirement mailed Mar. 29, 2013, 9 pgs.
International Application Serial No. PCT/US2011/053492, International Preliminary Report on Patentability mailed Apr. 11, 2013, 11 pgs.
International Application Serial No. PCT/US2011/053492, International Search Report mailed Mar. 5, 2012, 7 pgs.
International Application Serial No. PCT/US2011/053492, Invitation to Pay Additional Fees and Annex to Partial International Search Report mailed Jan. 17, 2012, 7 pgs.
International Application Serial No. PCT/US2011/053492, Written Opinion mailed Mar. 5, 2012, 9 pgs.
Kujala, Sauli, et al., "Effect of porosity on the osteointegration and bone ingrowth of a weight-bearing nickel-titanium bone graft substitute", Biomaterials, 24, (2003), 4691-4697.
U.S. Appl. No. 13/246,544, Advisory Action mailed Mar. 21, 2014, 3 pgs.
U.S. Appl. No. 13/246,544, Response filed Mar. 5, 2014 to Final Office Action mailed Jan. 6, 2014, 9 pgs.

\* cited by examiner

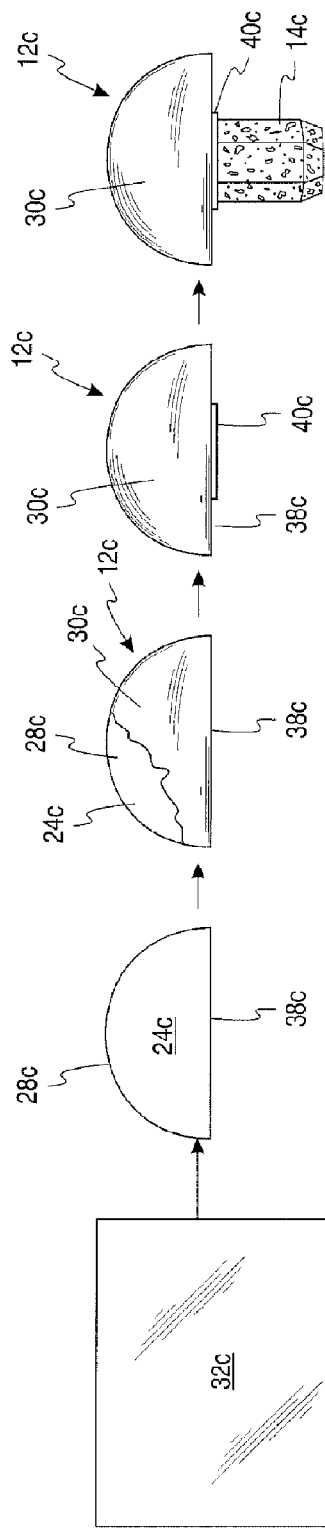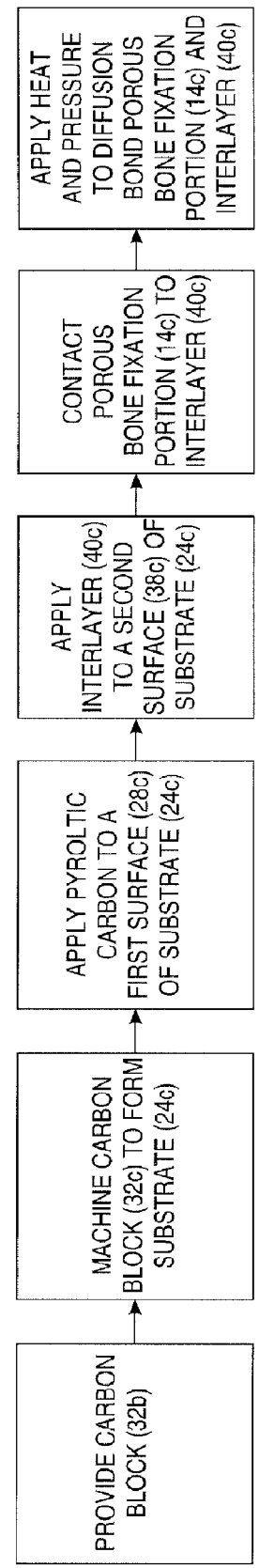
Fig. 11a
Fig. 11b

US 9,192,476 B2

PYROLYTIC CARBON IMPLANTS WITH POROUS FIXATION COMPONENT AND METHODS OF MAKING THE SAME

CROSS REFERENCE TO RELATED APPLICATION(S)

This application is a continuation of U.S. patent application Ser. No. 13/246,544, filed on Sep. 27, 2011, which claims the benefit of U.S. Provisional Application Ser. No. 61/387,678, filed Sep. 29, 2010, which are hereby incorporated by reference in its entirety.

FIELD OF THE DISCLOSURE

The present disclosure generally relates to prosthetic orthopedic implants, and more particularly to prosthetic orthopedic implants for use in bone joints and methods of making the same. Even more particularly, the present disclosure relates to prosthetic orthopedic implants that include a pyrolytic carbon bearing or articulating surface and a porous bone fixation structure.

BACKGROUND

Pyrolytic carbon has gained a lot of interest over the past few years as a bearing material in orthopedic applications. The material shows excellent wear characteristics, a modulus of elasticity similar to bone, and high strength. Pyrolytic carbon implants are commonly made by depositing a layer of pyrolytic carbon on a graphite substrate or core. Typically, pyrolytic carbon implants included a solid or non-porous bone fixation portion that is implanted into the bone and relies on a press-fit interference with surrounding bone tissue for fixation of the implant to the bone.

Bone on-growth or in-growth porous structures, such as porous tantalum and titanium structures, are sometimes used in orthopedic implants as the bone fixation component of the implant. Such porous structures are implanted into the bone and are designed to foster osseointegration. Osseointegration is the integration of living bone tissue within a man-made material. The porous structure and the bone material become intermingled as the bone grows into the pores. This intermingling of the bone tissue with the porous structure can enhance fixation between the orthopedic implant and the bone tissue. Because of the difficulties of bonding porous on-growth and in-growth structures to pyrolytic carbon and graphite surfaces, pyrolytic carbon implants have not included such porous fixation surfaces.

SUMMARY

In one aspect, the present disclosure is directed to an orthopedic implant including an articulation portion having a pyrolytic carbon bearing surface. The implant also includes a bone fixation portion extending from the articulation portion and having a porous structure configured for bone on-growth or bone in-growth.

In another aspect, a method of forming an orthopedic implant. The method includes providing a member having a first portion and a porous second portion. A layer of pyrolytic carbon is applied to a surface of the first portion and a metal is applied to the porous second portion.

In yet a further aspect, a method of forming an orthopedic implant that includes applying a layer of pyrolytic carbon to a first surface of a substrate and placing an interlayer comprising a metal between a second surface of the substrate and a porous metal structure. The porous metal layer, substrate and the interlayer are bonded together.

In yet another aspect, a method of forming an orthopedic implant including applying a layer of pyrolytic carbon to a first surface of a substrate and applying a metal interlayer to a second surface of the substrate. A porous metal structure is placed in contact with the metal interlayer, and a second outer layer of metal is applied to the substrate, interlayer and porous metal structure to bond the porous metal structure to the substrate.

In yet a further aspect, a method of forming an orthopedic implant includes applying a layer of pyrolytic carbon to a first surface of a substrate and applying an interlayer comprised of a metal to a second surface of the substrate. A metal sheet is then placed between the interlayer and a porous metal structure, and heat and pressure are applied to bond the metal structure, metal sheet and interlayer together.

BRIEF DESCRIPTION OF THE FIGURES

In the course of this description, reference will be made to the accompanying drawings, wherein:

FIG. 9b is a flow-chart showing the method illustrated in FIG. 7a;

FIG. 10b is a flow-chart showing the method illustrated in FIG. 8a;

FIG. 11a is a schematic illustration of yet another embodiment of a method of making an implant of the present disclosure;

FIG. 11b is a flow-chart showing the method illustrated in FIG. 9a;

DETAILED DESCRIPTION

As required, detailed embodiments of the present invention are disclosed herein; however, it will be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Generally, the prosthetic implants disclosed herein include an articulation portion having a pyrolytic carbon bearing or articulating surface and a porous bone in-growth or on-growth fixation structure or portion which is combined or otherwise associated with the articulation portion. Pyrolytic carbon is a brittle material that is biocompatible with bone and cartilage. It has good wear and strength properties and has been found to be a good bearing or articulating material for joint repair and replacement applications. The bearing surface of implants may articulate against, for example, natural body tissues, such as bone, or may articulate against a surface of an adjacent prosthetic component. Such implants are particularly useful in bone joint repair and replacement and may be used to treat or repair defects in, for example, the knee, hip, shoulder, fingers, elbow, toes or ankle. However, it will be appreciated that the use of such implants are not limited to joint repair or in connection with the joints specifically identified.

Figure 1:
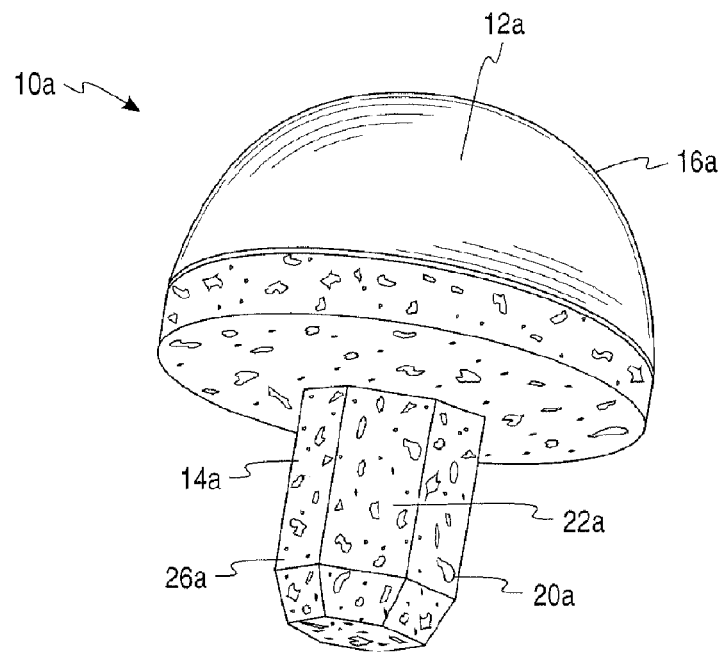
FIG. 1 is a perspective view of one embodiment of an implant of the present disclosure.
Figure 2:
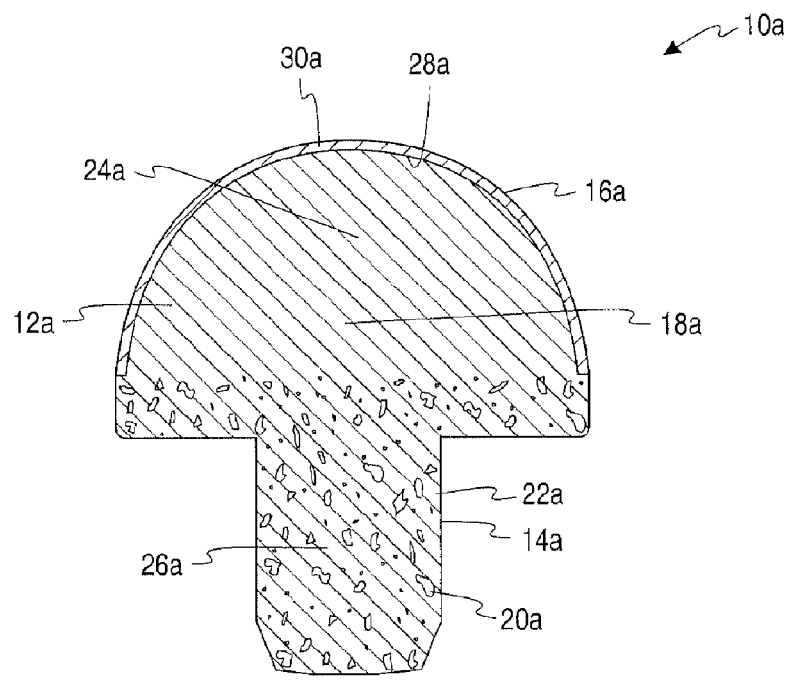
FIG. 2 is a cross-sectional view of the implant of FIG. 1.

Referring to FIGS. 1 and 2, implant 10a includes a first portion or articulation portion 12a associated with a second portion or bone fixation portion 14a. In the illustrated embodiment, the bone fixation portion 14a is shaped to be received into or implanted into a section of bone at the location of a joint and includes a porous bone in-growth or on-growth structure or region. The articulation portion 12a further includes a bearing surface 16a that is comprised of pyrolytic carbon and that functions as an articulating or bearing surface for the implant 10a. In the illustrated embodiment, the bearing surface 16a forms an outer layer or cover of the articulation portion 12a, and more specifically entirely covers an underlying body or substrate 24a (see FIG. 2). However, it will be appreciated that the bearing surface 16a may be sized to only cover a portion or multiple portions of the substrate 24a depending on the desired articulation points of the implant. Alternatively, the entire articulation portion 12a could be formed of pyrolytic carbon.

In the embodiment illustrated in FIGS. 1 and 2 and other figures contained herein, the articulation portion 12a is hemisphericaly shaped or ball-shaped. In this configuration, the articulation portion 12a may function, for example, as the articulating head or ball of a ball and socket joint commonly found in hip or shoulder. The articulation portion 12a of this and other embodiments described herein may be, however, designed for other joint functions, used in other types of joints, or even used for other orthopedic applications. Accordingly, the articulation portion 12a may take on any variety of suitable sizes and regular and irregular geometric shapes, depending on the application. For example, the articulation portion may be cubical, cylindrical, cup-shaped, etc. In addition, depending on the desired application, the bearing surface 16a may take on any variety of configurations, for example, concave.

The second or bone fixation portion 14a preferably includes a porous structure or region 26a in order to allow for bone in-growth or on-growth. In one embodiment, the bone fixation portion 14a may be made entirely or partially from a porous material or made to contain pores and more specifically surface pores 20a. Further, the bone fixation portion 14a includes a projection or stem element 22a that is sized and shaped to be implanted into bone. In the illustrated embodiment, the stem element 22a has a polygonal cross-section and, more particularly a hexagonal cross-section. In other embodiments, the stem element 22a may have other polygonal shapes or may be cylindrical, spherical, conical, or any other suitable configuration. In further embodiments, multiple projections or stem elements 22a may be incorporated to assist in limiting implant rotation or to provide different bone fixation arrangements.

When implanted within bone, the porous structure or region 26a of the bone fixation portion 14a and in particular the stem element 22a is receptive to bone cell and tissue on- and/or in-growth which enhances fixation of the implant 10a to the bone. The porous region 26a of the bone fixation portion 14a and the porous regions of the bone fixation portions of other embodiments described herein may have a pore size, pore interconnectivity, and/or other features that facilitate bone tissue on- and/or in-growth into the pores, as known in the art. Preferably, the bone fixation portion 14a is formed entirely from a highly porous material or a material adapted to be porous that may have a porosity as low as about 55, 65, or 75 percent by volume or as high as about 80, 85, or 90 percent by volume. However, it will be appreciated that the bone fixation portion 14a may not be entirely constructed of a porous material but includes region(s) comprised of porous materials positioned thereon.

Referring to FIG. 2, in this embodiment, the implant 10a has a core 18a that includes the body or substrate 24a of the articulation portion 12a and the porous section or region 26a of the bone fixation portion 14a. In one embodiment, the core 18a and consequently the substrate 24a and porous region 26a may be constructed out of a single material, for example, carbon, and more particularly, a dense, isotropic graphite. As such, the substrate 24a and the porous stem element 22a may be of a one-piece or unitary body or construction.

In order to enhance the visibility of the implant or portions thereof under fluoroscopy or x-ray imaging, the carbon may be doped with or otherwise include any suitable radiopacifiers, such as tungsten, zirconia or barium sulphate. In the embodiment illustrated in FIG. 2, the substrate 24a includes an exterior surface 28a that has pyrolytic carbon layer 30a positioned at least partially thereon. The pyrolytic carbon layer 30a helps form the bearing surface 16a of articulation portion 12a. It shall be appreciated that core 18a also may be constructed out of any other suitable material that can have pyrolytic carbon applied thereto and is suitable for use in orthopedic applications.

The pyrolytic carbon layer 30a may be applied to the substrate 18a by any suitable method known in the art. For example, the pyrolytic carbon layer 30a may be applied by chemical vapor deposition (CVD) or physical vapor deposition (PVD). In the embodiment shown in FIG. 2 and other embodiments described herein, the pyrolytic carbon layer 30a has a uniform thickness. The thickness of the pyrolytic carbon layer 30a, however, may vary to accommodate particular applications of the implant. Preferably, the pyrolytic carbon layer 30a has a thickness of at least about 50 μm. In other embodiments, the pyrolytic carbon layer 30a has a thickness of at least about 200 μm, 300 μm, 400 μm or 500 μm. In other embodiments, the pyrolytic carbon layer is between about 500 μm and 1000 μm.

Referring back to bone fixation portion 14a, in this embodiment, the bone fixation portion 14a comprises porous region 26a of the core 18a. As explained in more detail below, porous region 26a of core 18a may be formed by drilling or machining holes or pores 20a or a matrix of holes or pores into and/or through the porous region 26a. The resultant holes or pores 20a of porous region 26a may then be infiltrated and coated with a coating, such as a metal coating, to promote bone in-growth or on-growth, as described in more detail below. In one embodiment, the pores 20a pass through the entire bone fixation portion 14a. In other embodiments, the pores 20a are created to a porous region that extends between about 500 um and 4000 um and preferably between about 1000 um and 2000 um from the outer surface and into the bone fixation portion 14a. Alternatively, as discussed below with respect to FIGS. 7 and 8, the porous region 26a could be constructed out of a material with the desired porosity and attached or applied to the core.

Figure 9A:
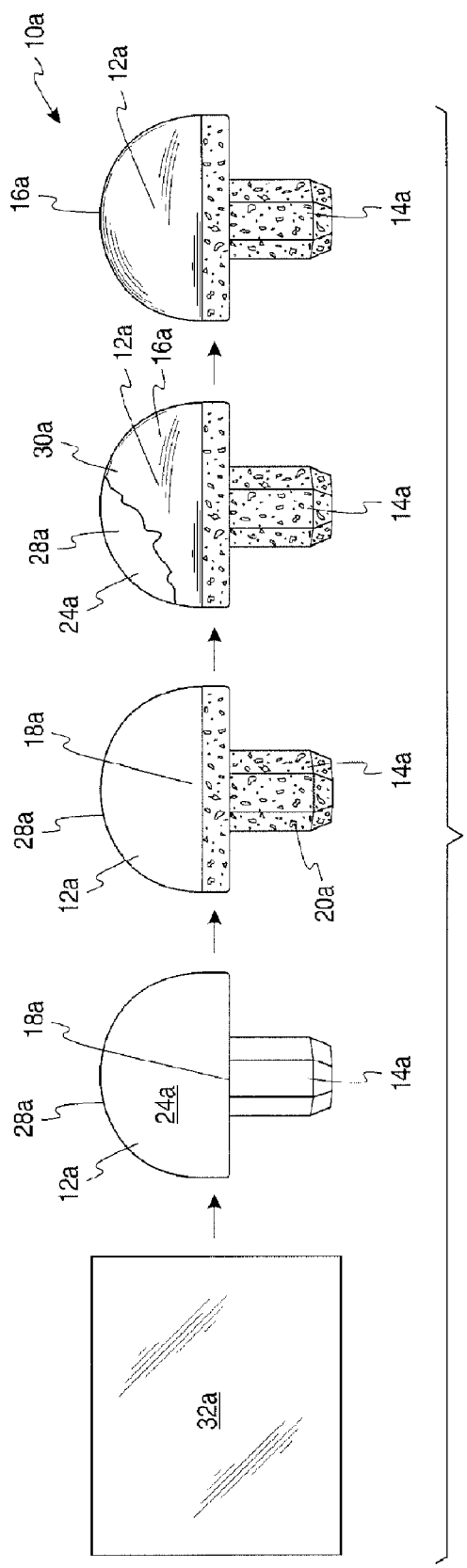
FIG. 9a is a schematic illustration of one embodiment of a method of making an implant of the present disclosure.
Figure 9B:
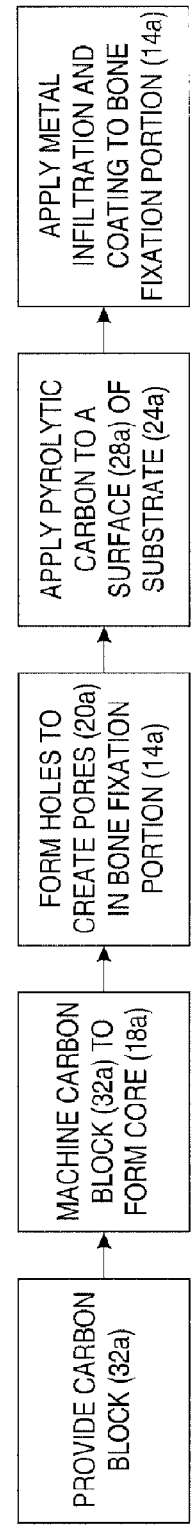

A schematic illustration and flowchart of one embodiment of a method of making the implant 10a illustrated in FIGS. 1 and 2 are shown in FIGS. 9a and 9b, respectively. It is understood that the steps of the method may be carried out in any suitable order which results in an implant fit for its desired orthopedic use. In one step, a block of carbon 32a, preferably a dense, isotropic graphite, is machined or otherwise processed into a desired shape to form the core 18a of implant 10a. In the embodiment shown, the block 32a is machined into a core 18a having a substrate 24a and a bone fixation portion 14a. The substrate 24a at least partially forms the articulation portion 12a. Holes or pores 20a or a matrix of holes or pores are then created in the bone fixation portion 14a of the core 18a, resulting in a porous region 26a of bone fixation portion 14a. In one embodiment, the bone fixation portion 14a is drilled or otherwise machined to create holes 20a in porous region 26a.

In another step, the bone fixation portion 14a is masked or otherwise protected or covered leaving substrate 24a of core 18a exposed and a pyrolytic carbon layer 30a is applied to the outer surface 28a of substrate 24a. The pyrolytic carbon layer 30a may be applied by any suitable process. In one embodiment, the pyrolytic carbon layer 30a is applied by CVD. In yet another step, the articulation portion 12a/substrate 24a is masked or otherwise protected and covered leaving the bone fixation portion 14a and more particularly the porous region 26a exposed and a coating is applied to at least a portion of the porous region 26a so that the coating infiltrates the holes 20a and coats the porous regions 26a of second portion 14a. In one embodiment, the coating is a metal such as but not limited to, tantalum, titanium, niobium, alloys of the same or any other suitable metal or alloy. Further, the metal may be applied to the porous regions 26a by, for example, CVD, PVD or any other suitable process. Other examples of coatings include bone on-growth or in-growth coatings such as hydroxyapatite or forms of calcium phosphate.

The resulting implant 10a includes a articulation or first portion 12a including a pyrolytic carbon bearing surface 16a and second or bone fixation portion 14a having a porous structure or region 26a that is suitable for bone cell and tissue on- and/or in-growth.

Figure 3:
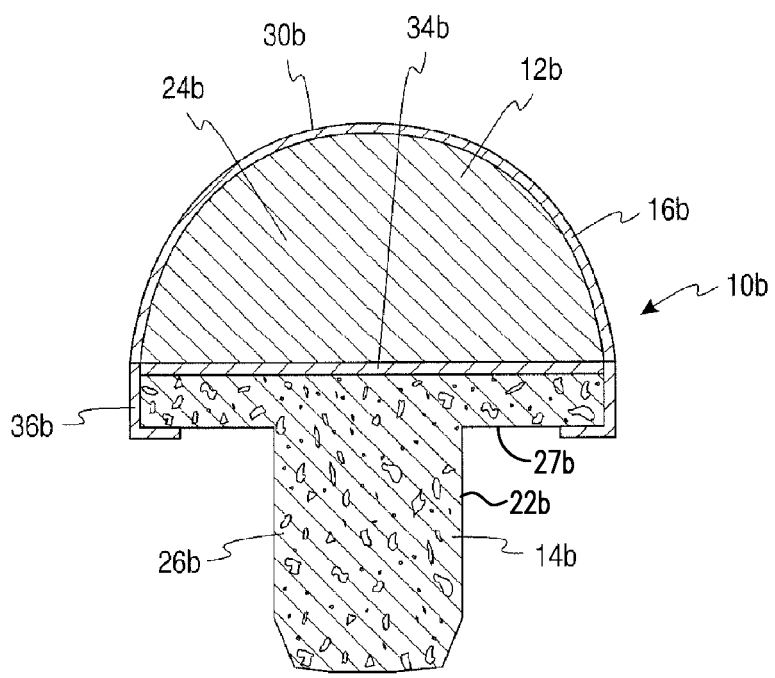
FIG. 3 is a cross-sectional view of another embodiment of an implant of the present disclosure.

FIG. 3 illustrates another embodiment of an implant 10b of the present disclosure which includes an articulation or first portion 12b and a second or bone fixation portion 14b with a porous region 26b. Similar to the previous embodiment, the articulation portion 12b includes a body or substrate 24b having a pyrolytic carbon layer 30b thereon that forms the bearing surface 16b. The substrate 24b may be made of any material or combination of materials suitable for having pyrolytic carbon applied thereto and in one embodiment the substrate 24b is carbon, preferably a dense, isotropic graphite. Additionally, in order to enhance the visibility of the implant or portions thereof under fluoroscopy or x-ray imaging, the carbon may be doped with or otherwise include any suitable radiopacifiers, such as tungsten, zirconia and barium sulphate.

In this embodiment, the bone fixation portion 14b comprises a porous structure preferably constructed out of metal. The bone fixation portion 14b is separately formed and is not unitary with the substrate 24b. The bone fixation portion 14b may be made of any suitable porous bone on- or in-growth metal structure known in the art. For example, the bone fixation portion 14b may be made of Trabecular Metal®, generally available from Zimmer, Inc. of Warsaw, Ind. Such material may be formed from a reticulated vitreous carbon foam substrate which is infiltrated and coated with a metal, such as tantalum, titanium, niobium, alloys of the same or any other suitable metal or alloy, by a CVD process in the manner disclosed in U.S. Pat. No. 5,282,861. The porous metal structure may have a pore size, pore interconnectivity, and/or other features that facilitate bone tissue on- and/or in growth.

As described in more detail below, the bone fixation portion 14b is bonded or otherwise attached to the substrate 24b of the articulation portion 12b by a metal interlayer 34b and/or a metal outer layer 36b. The metal interlayer 34b may be a layer of metal deposited or otherwise placed on a surface of substrate 24b or may be a sheet or foil positioned between substrate 24b and bone fixation portion 14b. Preferably, metal interlayer 34b and metal outer layer 36b are constructed out of the same metal or alloy as that of the bone fixation portion 14. It should be noted that the thicknesses of metal interlayer 34b and metal outer layer 36b are not drawn to scale in the figures, but have been exaggerated for illustrative purposes. Such interlayer 34b may have a thickness of between about 100 um and about 1 mm, and more preferably between about 400 um and about 600 um. The outer layer 36b may have a thickness of between about 50 um and about 400 um, and more preferably between about 150 um and about 250 um. However, it will be appreciated that the thicknesses may be altered in order to obtain the desired implant properties.

Figure 10A:
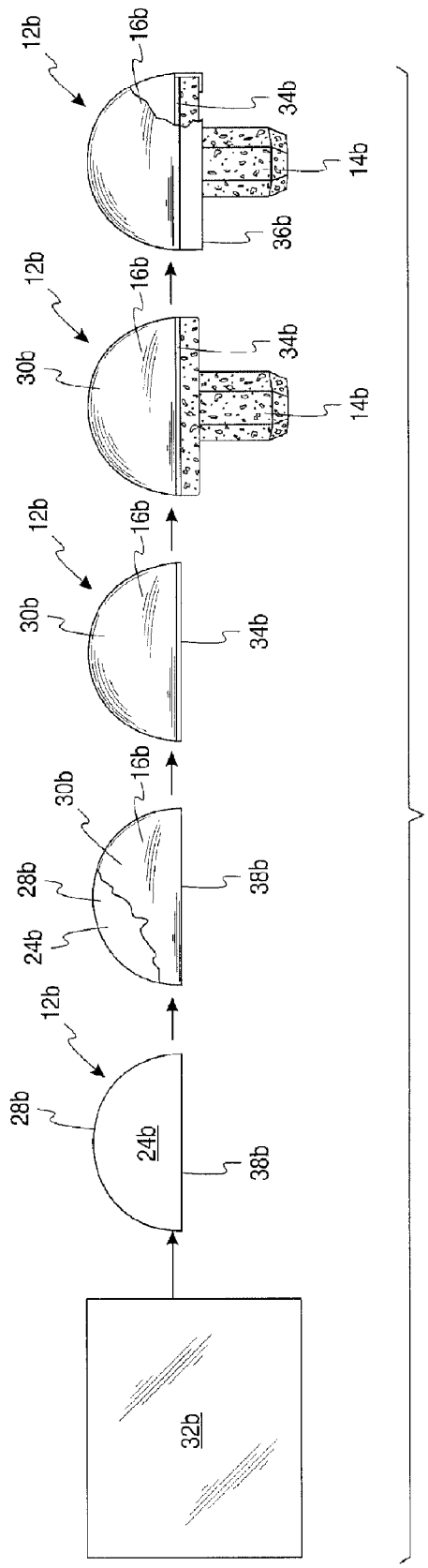
FIG. 10a is a schematic illustration of another embodiment of a method of making an implant of the present disclosure.
Figure 10B:
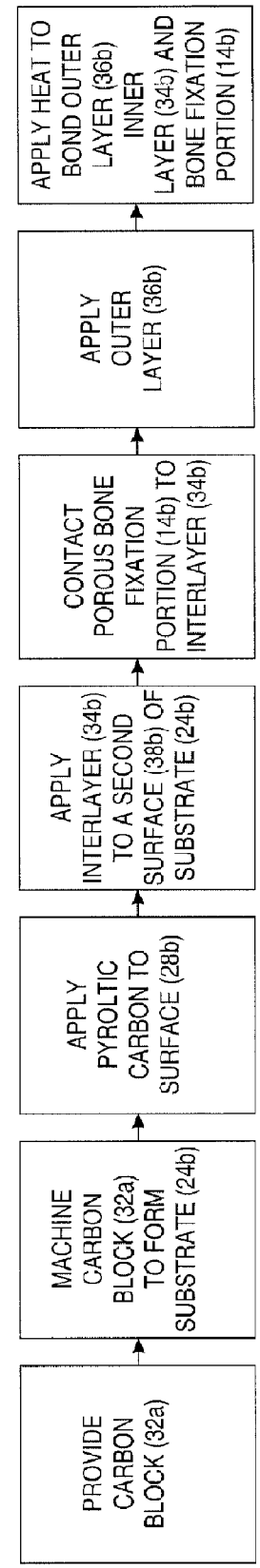

A schematic illustration and flowchart showing one embodiment of a method of making implant 10b are shown in FIGS. 10a and 10b, respectively. It is understood that the steps of the method may be performed in any order that produces an implant suitable for use in orthopedic applications. A block of carbon 32b, preferably a dense, isotropic or fiber reinforced graphite, is machined or otherwise processed to form the substrate 24b of articulation portion 12b of the implant 10b. In order to form bearing surface 16b, a pyrolytic carbon layer 30b is applied to an outer surface 28b of substrate 24b by any suitable method known in the art. For example, the pyrolytic carbon layer may be applied by CVD.

An interlayer 34b, preferably metallic and more specifically, a tantalum or titanium interlayer, is applied to outer surface 38b of the substrate 24b. The metal interlayer 34b may be applied by any suitable method known in the art, such as CVD or PVD. Further, the metal interlayer 34b may be formed of a metal foil or sheet. Undercuts, holes and/or other surface deviations may be located or formed in substrate 24b, and particularly in outer surface 38b, so that when the metal interlayer 34b is applied to outer surface 38b, the metal enters and engages the undercuts, holes, etc. to form a mechanical interlock between the interlayer 34b and substrate 24b.

The bone fixation portion 14b, which is comprised of a porous metal structure and preferably a porous tantalum structure, is placed against the metal interlayer 34b. A metal outer layer 36b, preferably a tantalum metal outer layer, is applied to the bone fixation portion 14b, the metal interlayer 34b, and substrate 24b/articulation portion 12b. Again, the substrate 24b may include undercuts, holes or other deviation so that when outer layer 36b is applied, the metal may engage and enter such undercuts, holes or other deviations in the surface to create a mechanical interlock. Preferably, but not necessarily, the interlayer 34b, outer layer 36b and bone fixation portion 14b are all constructed of the same metal. After the outer layer 36b has been applied, the metal interlayer 34b, metal outer layer 36b and bone fixation portion 14b are subjected to elevated temperatures to bond the bone fixation portion 14b to substrate 24b and form the implant 10b.

Figure 4:
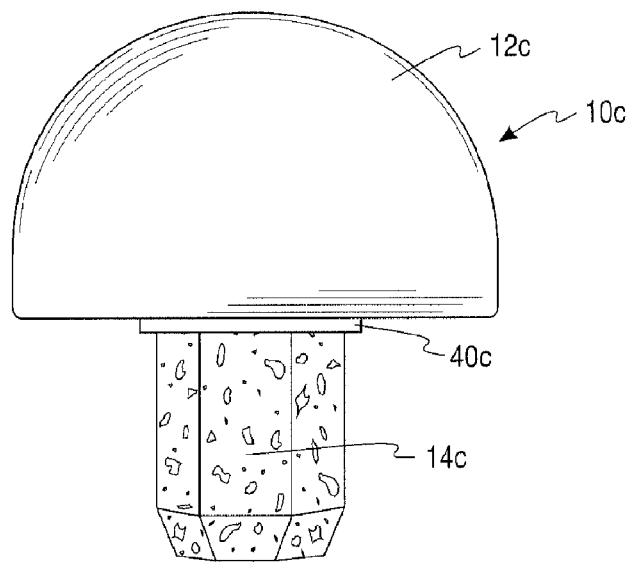
FIG. 4 is an elevation view of yet another embodiment of an implant of the present disclosure.
Figure 5:
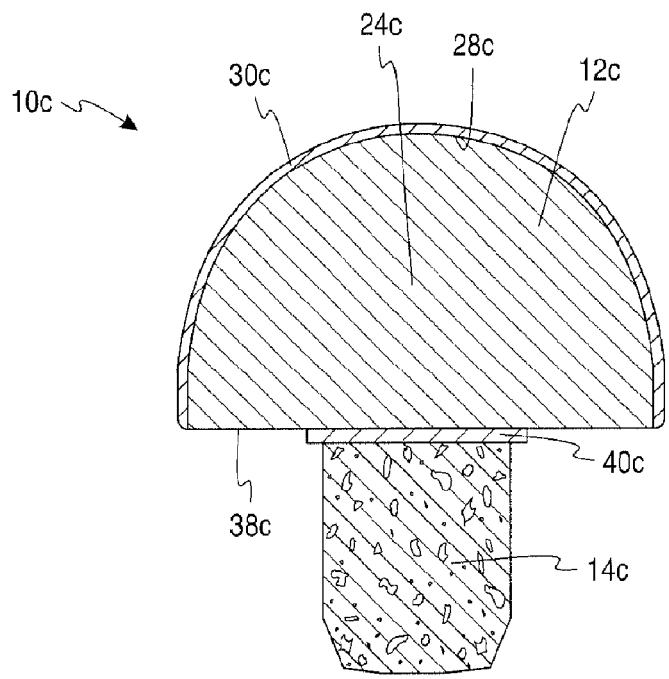
FIG. 5 is a cross-sectional view of the implant of FIG. 4.

FIGS. 4 and 5 illustrate another embodiment of an implant 10c of the present disclosure. Similar to the other embodiments, the implant 10c includes a articulation or first portion 12c and a bone fixation or second portion 14c. Referring to FIG. 5, the articulation portion 12c includes a body or substrate 24c. The substrate 24c includes a surface 28c having a pyrolytic carbon layer 30c positioned thereon. The substrate 24c may be made of any material or combination of materials suitable for having pyrolytic carbon applied thereto and in one embodiment the substrate 24c is carbon, preferably a dense, isotropic or fiber reinforced graphite. Additionally, in order to enhance the visibility of the implant or portions thereof under fluoroscopy or x-ray imaging, the carbon may be doped with or otherwise include any suitable radiopacifiers, such as tungsten, zirconia or barium sulphate.

Bone fixation portion 14c may be made of any suitable porous bone on- or in-growth metal structure described herein or known in the art. Alternatively, the bone fixation portion could be constructed of a material that could be made porous through any method known in the art. The porous bone fixation portion 14c is bonded to the substrate 24c using interlayer 40c. Interlayer 40c is preferably a metal that is readily soluble with the metal of the porous stem 14c. As explained in more detail below, interlayer 40c may be applied to surface 38c of the substrate 24c by any suitable deposition process, such as CVD or PVD. Undercuts, holes and/or other surface deviations may be located in substrate 24b, and particularly in surface 38c, so that when the metal interlayer 40c is applied to surface 38c, the metal enters and engages the undercuts, holes, etc. to form a mechanical interlock between the metal interlayer 40c and substrate 24c. In another embodiment, the interlayer 40c may be a metal sheet or foil.

Figure 6:
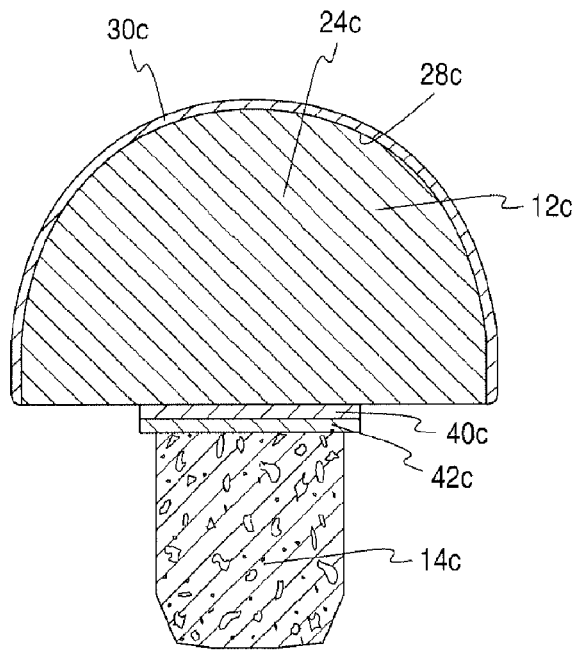
FIG. 6 is a cross-sectional view of another embodiment of an implant of the present disclosure.

In a further embodiment, as shown in FIG. 6, the implant 10c may include both a deposited interlayer 40c and a thin interlayer such as a metal foil or sheet 42c located between bone fixation portion 14c and substrate 24c to assist in the bonding process. It should be noted that the thicknesses of metal interlayer 40c and metal foil 42c are not drawn to scale in the figures, but have been exaggerated for illustrative purposes. The interlayer 40c may have a thickness of between about 100 um and about 1000 um, and more preferably between about 400 um and about 600 um. The foil sheet 42c may have a thickness of between about 100 um and about 1000 um, and more preferably between about 400 um and about 600 um.

A schematic illustration and flowchart showing one embodiment of a method of making the implants 10c illustrated in FIGS. 5 and 6 are shown in FIGS. 11a and 11b, respectively. The steps of the method described herein may be performed in any order that produces an implant suitable for use in orthopedic applications. A block of carbon 32c, preferably a dense, isotropic graphite, is machined or otherwise processed to form the substrate 24c of articulation portion 12c of the implant. A pyrolytic carbon layer 30c is applied to an outer surface 28c of the substrate 24c. A metal interlayer 40c, preferably comprised of a metal that is readily soluble with the metal of the porous metal second portion 14c, is applied to surface 38c of substrate 24c. In one embodiment, the metal interlayer is comprised of titanium. The metal interlayer 40c may be applied by any suitable process know in the art, such as CVD. Undercuts, holes or other surface deviations may be located in the substrate 24c, and in particular surface 38c, so that when the metal interlayer 40c is applied to the substrate 24c, the metal enters and engages the undercuts, holes, etc. to form a mechanical interlock between the metal interlayer 40c and substrate 24c. In another embodiment, interlayer 40c is a metal foil or sheet.

A bone fixation portion 14c comprised of a porous metal structure, such as any of the porous metal structures described herein or known in the art, is placed against the metal interlayer 40c to form an assembly. In one embodiment, one of the porous bone fixation portion 14c and the interlayer 40c is comprised of tantalum and the other one is comprised of titanium. Optionally, an interlayer such as a metal foil or sheet (not shown) may be placed between the porous metal bone fixation portion 14c and a deposited metal interlayer 34c so that the implant includes both a deposited metal interlayer 40c and a metal foil or sheet. In one embodiment the metal foil or sheet is constructed out of the same metal as the interlayer 34c.

Heat and pressure are applied to the assembly for a period of time sufficient to induce solid state diffusion between the interlayer 40c and porous metal bone fixation portion 14c, and, if used, the metal foil or sheet. As is known to those skilled in the art, solid-state diffusion is the movement and transport of atoms in solid phases. Solid-state diffusion bonding forms a joint through the formation of bonds at an atomic level due to transport of atoms between two or more metal surfaces. Heat and pressure may be supplied to the assembly by a variety of methods known in the art. For example, the assembly may be heated electrically, radiantly, optically, by induction, by combustion, by microwave, or any other suitable means known in the art. Pressure may be applied mechanically by clamping the assembly together prior to insertion of the assembly into a furnace, or pressure may be applied via a hot pressing system capable of applying pressure once the assembly reaches a target temperature, as is known in the art. Furthermore, hot pressing may include hot isostatic pressing, also known in the art. In one embodiment, the assembly is clamped and heated to at least about 940° C. for 4 hours in a vacuum or in another sub-atmospheric pressure of an inert atmosphere.

Preferably, the clamped assembly is heated to less than the melting temperature of the components. The time required to achieve bonding may be as little as less than 1 hour and as long as about 48 hours, and will depend on the metals involved, the temperatures, atmosphere and the pressures applied. After the diffusion process has been completed, the implant is formed.

Figure 7:
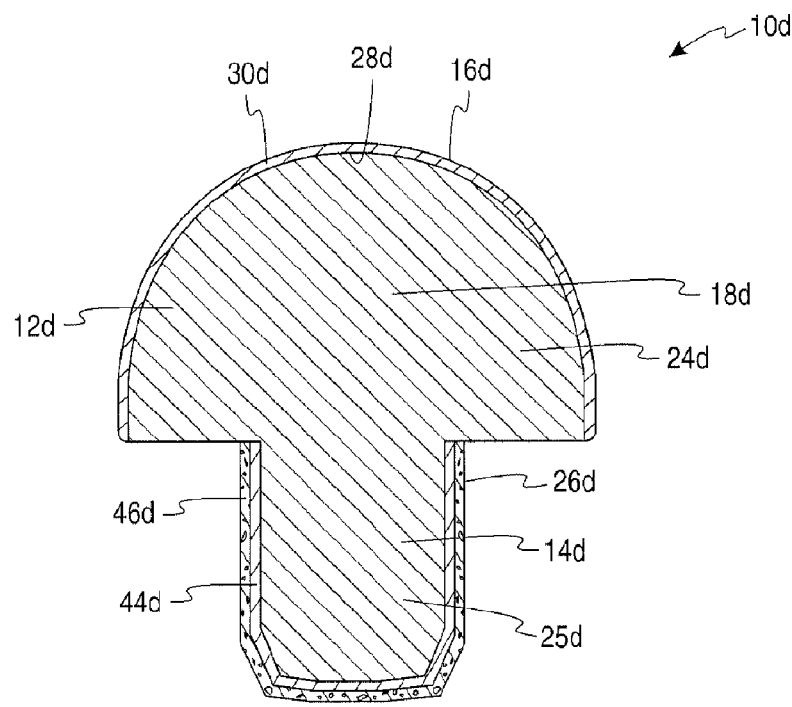
FIG. 7 is a cross-sectional view of still yet another embodiment of an implant of the present disclosure.

Yet another embodiment of an implant 10d of the present disclosure is illustrated in FIG. 7. Implant 10d includes a core 18d that defines a substrate 24d for an articulation portion 12d and a substrate 25d for a bone fixation portion 14d. Similar to other embodiments disclosed herein, the substrate 24d of the articulation portion 12d has a pyrolytic carbon layer 30d thereon that forms the bearing surface 16d. The core 18d may be made of any material or combination of materials suitable for having pyrolytic carbon applied thereto and in one embodiment the substrate 24d is carbon, preferably a dense, isotropic graphite. Additionally, in order to enhance the visibility of the implant or portions thereof under fluoroscopy or x-ray imaging, the carbon may be doped with or otherwise include any suitable radiopacifiers, such as tungsten.

The bone fixation portion 14d further includes a porous exterior layer 46d overlaying at least a portion of substrate 25d of core 18d to form porous region 26d. The exterior layer 46d may be made of any suitable porous bone on- or in-growth material known in the art. For example, the exterior layer 46d may be made of metal structure such as but not limited to titanium or tantalum. However, it will be appreciated that other materials may be used depending upon the desired characteristics of the implant. The porous region 26d may have a thickness, pore size, a pore interconnectivity, and/or other features that facilitate bone tissue on- and/or in growth. In one embodiment, the exterior layer 46d/porous region 26d may have a thickness of between about 5 um and about 300 μm. In order to facilitate the bonding of the exterior layer 46d to the substrate 24d, the bone fixation portion 14d may include an intermediate layer 44d. In the embodiment illustrated in FIG. 7, the intermediate layer 44d is formed from a metal such as titanium that is applied via CVD or PVD onto the substrate 25d of core 18d. The intermediate layer 44d may have a thickness of up to about 1 mm.

Figure 12:
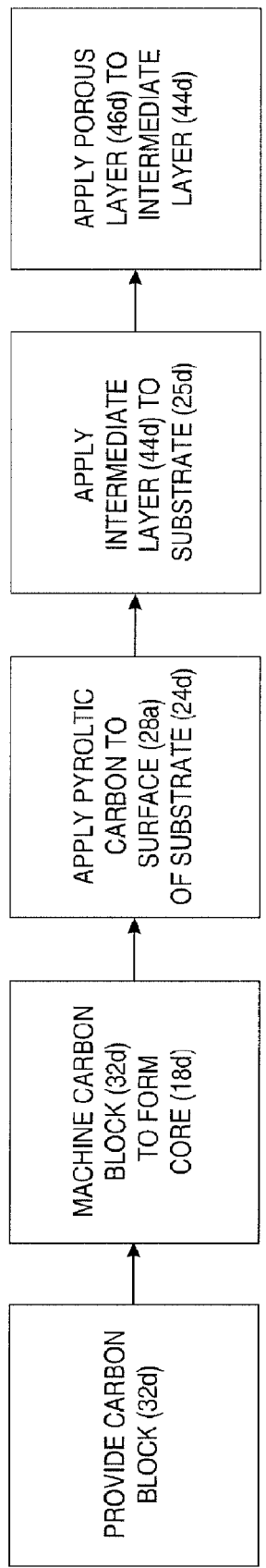
FIG. 12 is a flow-chart of one embodiment of a method of making an implant of the present disclosure.

FIG. 12 is a flowchart showing one embodiment of a method of making the implant 10d illustrated in FIG. 7. The steps of the method described herein may be performed in any order that produces an implant illustrated in FIG. 7. In one step, a block of carbon, preferably a dense, isotropic graphite, is machined or otherwise processed to form core 18d with substrate 24d and substrate 25d. In another step, a pyrolytic carbon layer 30d is applied to the outer surface 28d of substrate 24d of the articulation portion 12d. An intermediate layer 44d, preferably comprised of a metal that can adhere to the graphite substrate 24e is applied, preferably via CVD or PVD, to an outer surface of the substrate 25d of the bone fixation portion 14d. The exterior porous layer 46d is applied to the intermediate layer 44d, preferably via plasma spraying. However, it will be appreciated that any other suitable method of attaching the exterior layer 46d to the intermediate layer 44d or directly to the substrate 25d if the intermediate layer is omitted may be used. The bearing surface 16d of the pyrolytic carbon layer 30d may be polished or otherwise treated or conditioned in order to obtain a generally smooth articulating surface.

Figure 8:
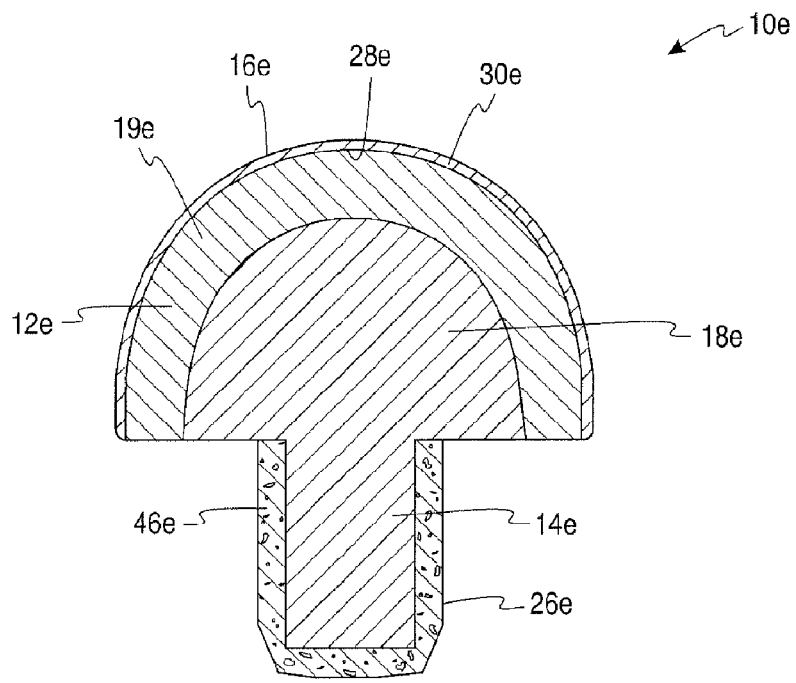
FIG. 8 is a cross-sectional view of another embodiment of an implant of the present disclosure.

Turning to FIG. 8, implant 10e is another embodiment of an orthopedic device of the present disclosure and is similar to the other implants disclosed herein. Implant 10e includes a metallic core 18d, such as but not limited to titanium or tungsten, that partially defines an articulation portion 12e and bone fixation portion 14e. The articulation portion 12e has a pyrolytic carbon layer 30e thereon that forms the bearing surface 16e. An intermediate layer 19e is positioned between the pyrolytic carbon layer 30e and the core 18. The intermediate layer 19e is preferably constructed out of a material, such as carbon, preferably a dense, isotropic graphite, that can bond or otherwise adhere to the metal core 18e and pyrolytic carbon layer 30e. The core 18e also forms the interior portion of the bone fixation portion 14e and is at least partially surrounded by a porous exterior layer 46e that forms the porous region 26e. In the illustrated embodiment, the exterior layer 46e is made of a metal such as but not limited to porous titanium or tantalum metal structures. In one embodiment, the exterior layer 46e is Trabecular Metal®, generally available from Zimmer, Inc. of Warsaw, Ind. It will be appreciated, however, that other materials for the exterior layer 46e may be used depending upon the desired characteristics of the implant. The exterior layer 46e/porous region 26e preferably have a thickness, pore size, a pore continuity, and/or other features that facilitate bone tissue on- and/or in growth.

Figure 13:
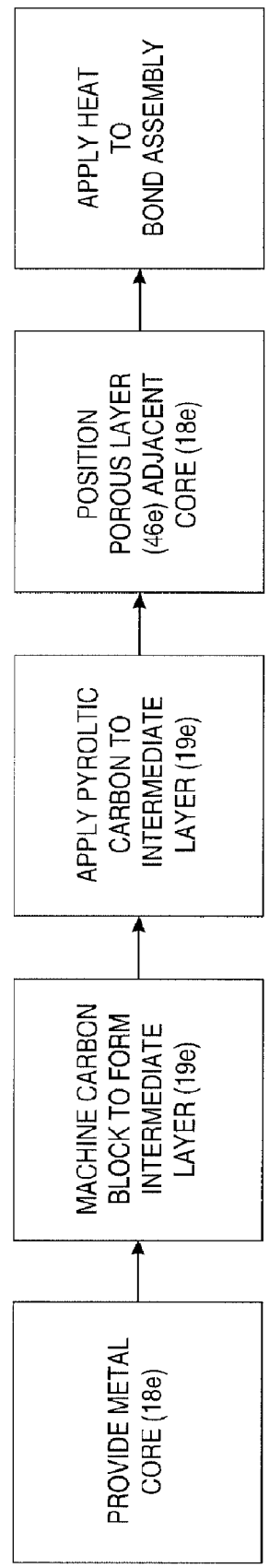
FIG. 13 is a flow-chat of another embodiment of a method of making an implant of the present disclosure.

FIG. 13 is a flowchart showing one embodiment of a method of making the implant 10e illustrated in FIG. 8. The steps of the method described herein may be performed in any order that produces an implant illustrated in FIG. 8. In one step, the metallic core is formed to the desired shape using a metal such as but not limited to titanium or tungsten. In another step, a block of carbon, preferably a dense, isotropic graphite, is machined or otherwise processed to form the intermediate layer 19e. The core 18e and intermediate layer 19e are positioned adjacent one another. Heat and pressure are applied to the assembly for a period of time sufficient to induce solid state diffusion between the core 18e and intermediate layer 19e. In another step, a pyrolytic carbon layer 30e is applied to the outer surface 28e of the intermediate layer 19e. The bearing surface 16e of the pyrolytic carbon layer 30e may be polished or otherwise treated or conditioned in order to obtain a generally smooth articulating surface. An exterior layer 46e is applied to the core 18e of the bone fixation portion 14e to form the porous region 26e. The exterior layer 46e is preferably comprised of a metal that can adhere to the material of the core 18e. in one embodiment, the exterior layer 46e comprised of a metal such as titanium is applied to the core 18e, preferably via plasma spaying. Alternatively, the exterior layer 46e may be comprised of a porous tantalum metal structure such as Trabecular Metal®, generally available from Zimmer, Inc. of Warsaw, Ind. In this embodiment, the metal exterior layer 46e may be positioned adjacent the core 18e. Heat and pressure are applied to the assembly for a period of time sufficient to induce solid state diffusion between the metal exterior layer 46e and the core 18e. It will be appreciated that bonding of the core 18e and intermediate layer 19e to one another and the exterior layer 46e to the core 18e could be formed in either a single step or two step process.

It will be understood that the methods, compositions, devices and embodiments described above are illustrative of the applications of the principles of the subject matter disclosed herein. It will also be understood that certain modifications may be made by those skilled in the art without departing from the spirit and scope of the subject mater disclosed and/or claimed herein. Thus, the scope of the invention is not limited to the above description, but is set forth in the following claims and/or any future claims made in any application that claims the benefit of this application.

What is claimed is:

1. A method of forming an orthopedic implant, comprising:
providing or obtaining an implant core constructed as a single implant piece, said implant core including an articulation portion and a bone fixation portion, wherein only part of said bone fixation portion is porous for receiving to tissue ingrowth, said part including a porous region with a porosity of 55% to 90% which includes surface pores; and
applying a layer of pyrolytic carbon to an outer surface of the articulation portion.

2. The method of claim 1, wherein said applying includes chemical vapor depositing the layer of pyrolytic carbon.

3. The method of claim 2 further comprising masking said bone fixation portion before applying the layer of pyrolytic carbon to the outer surface of the articulation portion.

4. The method of claim 1 further comprising applying a coating to said bone fixation portion, wherein said coating infiltrates pores in said bone fixation portion.

5. The method of claim 4, wherein said coating is a metal coating.

6. The method of claim 5, wherein said metal coating includes tantalum or a tantalum alloy.

7. The method of claim 1, wherein the bone fixation portion includes a stem element.

8. The method of claim 7, wherein the articulation portion forms an articulating head for use in a ball-and-socket joint.

9. The method of claim 1, wherein the porous region extends no more than 2000 μm into the bone fixation portion from an outer surface of the bone fixation portion.

10. The method of claim 1, wherein the implant core is constructed with carbon.

11. A method of forming an orthopedic implant, comprising:
providing or obtaining an implant core constructed as a single implant piece, said implant core including an articulation portion and a bone fixation portion, wherein only part of said bone fixation portion is porous for receiving tissue ingrowth, said part including surface pores; and applying a layer of pyrolytic carbon to an exposed outer surface of the articulation portion while a mask is masking said bone fixation portion.

12. The method of claim 11, wherein said part includes a porosity of 55% to 90%.

13. The method of claim 11, wherein said applying includes chemical vapor depositing the layer of pyrolytic carbon.

14. The method of claim 11 further comprising applying a coating to said bone fixation portion while a second mask is masking said articulation portion, wherein said coating infiltrates pores in said bone fixation portion.

15. The method of claim 14, wherein said coating is a metal coating.

16. The method of claim 11, wherein the implant core is constructed with carbon.

17. The method of claim 11, wherein the bone fixation portion includes a porous region that extends no more than 2000 µm into the bone fixation portion from an outer surface of the bone fixation portion.

18. A method of forming an orthopedic implant, comprising:
providing or obtaining an implant core constructed as a single implant piece, said implant core including an articulation portion and a bone fixation portion, wherein the entire bone fixation portion is porous with a porosity of 55% to 90%;
applying a layer of pyrolytic carbon to an exposed outer surface of the articulation portion while a mask is masking said bone fixation portion; and
applying a coating to said bone fixation portion while a second mask is masking said articulation portion, wherein said coating infiltrates pores in said bone fixation portion.

19. The method of claim 18, wherein the implant core is constructed with carbon.

20. The method of claim 18, wherein said coating is a metal coating.

21. A method of forming an orthopedic implant, comprising:
providing or obtaining an implant that includes an articulation portion and a bone fixation portion, wherein at least part of said bone fixation portion is porous for receiving tissue ingrowth;
applying a layer of pyrolytic carbon to an exposed outer surface of the articulation portion while a first mask is masking said bone fixation portion; and
applying a coating to said bone fixation portion while a second mask is masking said articulation portion, wherein said coating infiltrates pores in said bone fixation portion.

22. The method of claim 21, wherein said coating is a metal coating applied by chemical vapor deposition.

23. The method of claim 21, wherein the implant core is constructed with carbon.

\* \* \* \* \*